United States Patent [19]
Cardinaud et al.

[11] Patent Number: 6,077,967
[45] Date of Patent: Jun. 20, 2000

[54] METHOD FOR OBTAINING ORGANOSILANES USING A REDISTRIBUTION REACTION

[75] Inventors: Denis Cardinaud, Villeurbanne; Pascale Colin, Chassieu, both of France

[73] Assignee: Rhodia Chimie, Courbevoie, France

[21] Appl. No.: 09/381,659

[22] PCT Filed: Mar. 26, 1998

[86] PCT No.: PCT/FR98/00611

§ 371 Date: Nov. 30, 1999

§ 102(e) Date: Nov. 30, 1999

[87] PCT Pub. No.: WO98/43985

PCT Pub. Date: Oct. 8, 1998

[30] Foreign Application Priority Data

Mar. 27, 1997 [FR] France .................................. 97 04109

[51] Int. Cl.[7] ...................................................... C07F 7/08
[52] U.S. Cl. ............................................................ 556/469
[58] Field of Search ................................................ 556/469

[56] References Cited

U.S. PATENT DOCUMENTS

| 3,980,686 | 9/1976 | Lefort et al. ............................. 556/469 |
| 4,567,286 | 1/1986 | Lepage et al. ............................ 556/469 |
| 5,654,459 | 8/1997 | Kropfgans et al. ...................... 556/469 |
| 5,866,707 | 2/1999 | Herzig ..................................... 556/469 |

FOREIGN PATENT DOCUMENTS

| 0 652 221 | 5/1995 | European Pat. Off. . |
| 2 119 477 | 4/1972 | France . |
| 97 47629 | 12/1997 | WIPO . |

*Primary Examiner*—Paul F. Shaver
*Attorney, Agent, or Firm*—Burns, Doane, Swecker & Mathis, L.L.P.

[57] ABSTRACT

An improved redistribution reaction for the preparation of organosilanes wherein a silane or silicone resin is added after the reaction to inhibit the catalyst.

12 Claims, No Drawings

METHOD FOR OBTAINING ORGANOSILANES USING A REDISTRIBUTION REACTION

The subject-matter of the present invention is an improved method for obtaining organosilanes and the invention relates particularly to an improved method for obtaining organosilanes in which a so-called redistribution reaction is involved. More particularly, the present invention relates to an improved method for obtaining organosilanes in which is involved a redistribution reaction between a chlorinated organohydrosilane and an organosubstituted and optionally chlorinated silane, in order to result in a product comprising a redistributed chlorinated organohydrosilane, which is extracted from the reaction mixture by distillation.

Without this being limiting, the present invention is very especially targeted at a redistribution reaction between an alkylhydrodichlorosilane and a trialkylchlorosilane, in order to result in a product comprising a redistributed dialkylhydrochlorosilane. This redistributed dialkylhydrochlorosilane is a synthetic agent which is particularly valued in a great many varied applications, for example, preparation of organosilicon monomers or more condensed base compounds.

Dialkylhydrochlorosilane is one of the by-products from the synthesis of alkylchlorosilanes according to a conventional and well known procedure which consists in reacting alkyl chloride with silicon, in the presence of a copper catalyst, in order to form alkylchlorosilanes. In this synthesis, the dialkyldichlorosilane is the main product. Compounds of the trialkylchlorosilane, alkyltrichlorosilane and alkylhydrodichlorosilane type are also obtained, in addition to the abovetargeted dialkylhydrochlorosilane by-product.

Due to the industrial interest of these by-products in the chemistry of silicones and in particular of the dialkylhydrochlorosilane, such as dimethylhydrochlorosilane, numerous proposals for procedures for obtaining these by-products have seen the light of day. One of the few which has proved itself in this respect is that which consists in carrying out a redistribution reaction between, for example, an alkylhydrodichlorosilane and a trialkylchlorosilane or between an alkylhydrodichlorosilane and a tetraalkylsilane. This redistribution results in the targeted dialkylhydrochlorosilanes, which are extracted from the reaction mixture by distillation.

In this context, numerous redistribution reactions of organosilanes, cutting and redistributing silicon-alkyl, silicon-chlorine or silicon-hydrogen bonds, in the presence of various catalysts, such as Lewis acids, are known. French Patent FR-A-2,119,477 clearly illustrates this technique for the preparation of dialkylhydrochlorosilane by redistribution/distillation. In accordance with the teaching of this patent, methylhydrodichlorosilane and trimethylchlorosilane are reacted in a molar ratio of the order of 0.5 in the presence of a catalyst formed by $AlCl_3$. The reaction mixture is placed in a reactor, under an autogenous pressure of the order of 3 to $5 \times 10^5$ Pa, and maintained for several hours at a temperature of the order of 85 to 170° C. The Applicant Company has repeated this procedure of the prior art and it has observed that the yield of the distillation, which is carried out at the end of the process in order to separate the redistributed dimethylhydrochlorosilane from the reaction mixture, is abnormally low and peaks at approximately 71%. It must be considered that such results are unsatisfactory with regard to industrial profitability.

In this state of knowledge, one of the essential objects of the present invention consists of the development of an improved method for obtaining organosilanes in which is involved a redistribution reaction between a chlorinated organohydrosilane and an organosubstituted and optionally chlorinated silane, in order to result in a product comprising a redistributed chlorinated organohydrosilane, which is extracted from the reaction mixture by distillation, which method ought to be characterized by distillation yields of final targeted product, the redistributed chlorinated organohydrosilane, which are markedly superior to those of the known redistribution/distillation methods.

Another essential object of the invention is to provide a method of the type of that targeted above and which is particularly simple to carry out and is economical.

In order to be able to achieve all these objects, and others too, the Applicant Company has had the credit of demonstrating a side reaction phenomenon induced by the catalyst during the distillation. This is because it could be demonstrated that conventional redistribution catalysts, such as, for example, $AlCl_3$, catalyse a dismutation reaction of the chlorinated organohydrosilane produced by redistribution. Such a dismutation results in the conversion of the said redistribution product into by-products of the optionally chlorinated organohydrosilane type, on the one hand, and chlorinated organosilane type, on the other hand. That is how, for example, $Me_2HSiCl$ is converted to $Me_2SiH_2$ and to $Me_2SiCl_2$, due to this dismutation side reaction (the abbreviation Me denotes the monovalent $CH_3$ radical).

It is clear that such a phenomenon can only be entirely harmful to the yield of redistributed chlorinated organohydrosilane, such as, for example, $Me_2HSiCl$.

The credit of the Applicant Company has not been limited to this discovery of the technical problem existing in known redistribution/distillation reactions. This is because, entirely surprisingly and unexpectedly, it has also found a means of reducing, indeed eliminating, the dismutation side reaction by inhibiting the redistribution catalyst, once it has fulfilled its role in the first stage of the method.

It follows that the present invention relates to an improved method for obtaining organosilanes comprising:

a redistribution reaction between a chlorinated organohydrosilane of formula (1) $(R)_a(H)_bSiCl_{4-a-b}$ and an organosubstituted and optionally chlorinated silane of formula (2) $(R')_cSiCl_{4-c}$, in which formulae: a=1 or 2; b=1 or 2; a+b≦3; c=1, 2, 3 or 4; and the symbols R and R' are alike or different and each represent a linear or branched $C_1$–$C_6$ alkyl radical or a $C_6$–$C_{12}$ aryl radical; the said redistribution reaction taking place in the presence of an effective amount of a catalyst consisting of a Lewis acid of formula (3) $M(X)_d$, in which: M represents a metal selected from Ti, Fe, Cu, Ag, Zn, Cd, Hg, Al, Ga, In, B, Sn, Pb, Sb and Bi; X represents a halogen atom; and d represents the valency of the metal M;

and a separation by distillation of the chlorinated organohydrosilane produced by redistribution;

the said method being characterized in that, after the redistribution, at least one compound which inhibits the redistribution catalyst is introduced, this compound corresponding to the following definitions:

it is chosen from:
(i) a silane of formula:

$(R^1)_eSi(OR^2)_{4-e}$     (4)

in which:
the $R^1$ symbols are alike or different and each represent:
a hydrogen atom; a linear or branched $C_1$–$C_8$ alkyl radical optionally substituted by one or more halogen (s), such as, for example, methyl (Me), ethyl, propyl, butyl, octyl or 3,3,3-trifluoropropyl; a $C_5$–$C_8$ cycloalkyl radical, such as, for example, cyclohexyl or cycloheptyl; a $C_6$–$C_{12}$ aryl radical or an aralkyl radical having a $C_6$–$C_{12}$ aryl part and $C_1$–$C_4$ alkyl part which is optionally substituted on the aromatic part by one or more halogen(s), $C_1$–$C_3$ alkyl(s) and/or $C_1$–$C_3$ alkoxy (s), such as, for example, phenyl, xylyl, tolyl, benzyl, phenylethyl, chlorophenyl or dichlorophenyl;

the $R^2$ symbols are alike or different and each represent: a linear or branched $C_1$–$C_4$ alkyl radical; or a $C_6$–$C_{12}$ aryl radical;

e is 0, 1, 2 or 3;

(2i) a silicone resin having a viscosity at 25° C. at most equal to 5000 mPa·s and exhibiting the following distinctive features:

it has, in its structure, units chosen from those of formulae $(R^3)_3SiO_{0.5}$ (M), $(R^3)_2SiO$ (D), $R^3SiO_{1.5}$ (T) and $SiO_2$ (Q), at least one of these units being a T unit or a Q unit, in which formulae the $R^3$ symbols, which are alike or different, mainly have the definitions given above with respect to the $R^1$ symbols;

the proportions of the T and/or Q units, expressed by the number of T and/or Q units per 100 silicon atoms, are greater than 10%;

it also possesses, per molecule, —$OR^4$ end groups carried by silicon atoms of the M, D and/or T units, where:

the $R^4$ symbols, which are alike or different, each represent a hydrogen atom, a linear or branched $C_1$–$C_4$ alkyl radical or a $C_6$–$C_{12}$ aryl radical, the proportions of the —$OR^4$ ends, expressed by the mean number of these ends per 1 silicon atom, vary from 0.2 to 3;

it is used in proportions such that the ratio:

$$r = \frac{\text{number of moles of } M \text{ metal atoms contributed by the catalyst}}{\text{number of moles of } OR^2 \text{ or } OR^4 \text{ groups contributed by the inhibitor}}$$

is equal to or less than 1.1.

In accordance with the present invention, advantage is taken of the inhibition of the redistribution catalyst, once the latter has fulfilled its function. This neutralization of the catalytic activity makes it possible to reduce as much as possible, indeed eliminate, the dismuration side reactions which conventionally took place during the distillation. Thus, the targeted redistributed chlorinated organohydrosilanes are produced, at the end of distillation, with better yields than previously.

Another highly advantageous effect is observable when the inhibitor compound is used, which constitutes a preferred embodiment of the present invention, in proportions such that the ratio r mentioned above is situated very specifically within the range from 0.4 to 1.1.

This other highly advantageous effect consists of the elimination of the appearance and of the deposition of solid materials in the distillation residues, which then have a homogeneous look. In the case of the absence of inhibitor compound or in the case of the use of insufficient proportions of inhibitor compound (corresponding to values of r of greater than 1.1) or in the case of the use of excessively high proportions of inhibitor compound (corresponding to values of r of less than 0.4), the result is distillation residues which then have a two-phase look, due to the appearance and the deposition of solid materials. The Applicant Company believes that these solid materials may be: catalyst particles, in the case of the use of insufficient proportions of inhibitor compound; amorphous crystals of a complex formed from the catalyst and the inhibitor silicone compound, in the case of the use of excessively high proportions of inhibitor compound.

Examples of inhibitor silicone compounds which are well suited are:

as silanes (i): the alkoxysilanes of formula (4) in which:

the $R^1$ symbols, which are identical, each represent a linear or branched $C_1$–$C_4$ alkyl radical or a phenyl radical;

the $R^2$ symbols, which are identical, each represent a linear or branched $C_1$–$C_3$ alkyl radical;

e=1 or 2;

as resins (2i): the resins having a viscosity at 25° C. at most equal to 1000 mPa·s of MQ, MDQ, TD and MDT type, in the structure of which:

the $R^3$ symbols of the M, D and T units are alike or different and each represent a linear $C_1$–$C_4$ alkyl radical;

the proportions of the T and/or Q units are greater than 30%;

there are —$OR^4$ end groups where the $R^4$ symbol represents a hydrogen atom or a linear $C_1$–$C_2$ alkyl radical (the alkoxy radicals, when there are several of them, being identical to one another) and where the proportions of the said ends vary from 0.3 to 2.

The inhibitor silicone compounds which are very especially well suited are:

the alkoxysilanes (i) corresponding to the following

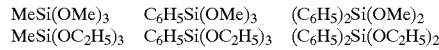

MeSi(OMe)₃   C₆H₅Si(OMe)₃   (C₆H₅)₂Si(OMe)₂
MeSi(OC₂H₅)₃ C₆H₅Si(OC₂H₅)₃ (C₆H₅)₂Si(OC₂H₅)₂ the resins (2i) of TD type, in the structure of which:

the $R^3$ symbols of the D units are methyl radicals, whereas the $R^3$ symbols of the T units are n-propyl radicals;

the proportions of the T units, expressed by the number of T units per 100 silicon atoms, lie within the range from 40 to 65% and those of the D units, expressed by the number of D units per 100 silicon atoms, lie within the range from 60 to 35%;

the —$OR^4$ end groups, where the $R^4$ symbol represents an ethyl radical, are carried by silicon atoms of the D and T units and are present in proportions ranging from 0.3 to 0.5.

The Lewis acids which are employed as catalysts in the present method are preferably chlorides and bromides.

Examples of catalysts which are highly suitable are: $TiCl_4$, $FeCl_3$, $CuCl$, $AgCl$, $ZnCl_2$, $AlCl_3$, $SnCl_2$, $BiCl_3$ and their various mixtures. The catalyst which is very especially well suited is $AlCl_3$.

The catalysts are used in proportions by weight generally ranging from 0.1 to 10% and preferably from 0.5 to 5% with respect to the total weight of the silanes of formulae (1) and (2) charged at the start. Proportions by weight which are very especially preferred are those ranging from 1 to 4% with respect to the same reference.

Another important parameter of the method according to the invention relates to the moment at which the inhibitor silicone compound is introduced. In any case, it is preferable for the latter to be introduced when the redistribution reaction is complete.

Furthermore, it being known that the redistribution reaction is generally carried out at temperatures of between 50° C. and 200° C. (advantageously under autogenous pressure) and that the reaction mixture is subsequently cooled before distillation, it is possible to anticipate introducing the inhibitor compound:

either at the redistribution temperature, before cooling, or after returning the reaction mixture to this cooling temperature, or before and after the said cooling.

In this context, the two preferred embodiments of the method according to the invention are given below:

According to a first embodiment:

the redistribution reaction is carried out at a temperature of between 50 and 200° C., preferably between 80 and 150° C., advantageously under autogenous pressure, the reaction mixture is subsequently cooled to a temperature of less than 40° C., preferably of less than 30° C. and more preferably still of between 10 and 30° C., the inhibitor silicone compound is then introduced, and, finally, the targeted chlorinated organohydrosilane, produced by redistribution, is separated by distillation.

According to a second embodiment:

the redistribution is carried out at a temperature of between 50 and 200° C., preferably between 80 and 150° C., advantageously under autogenous pressure, the inhibitor silicone compound is introduced, so that the redistribution is interrupted, the reaction mixture is subsequently cooled to a temperature of less than 40° C., preferably of less than 30° C. and more preferably still of between 10 and 30° C., and, finally, the targeted chlorinated organohydrosilane is separated by distillation.

As regards the parameters of the method (duration, temperature, pressure), it will be specified, to clarify our views, that it is highly advantageous for the redistribution temperature to be, for example, of the order of 90 to 120° C., while the ideal pressure is based around from 3 to $5 \times 10^5$ Pa. The duration of the redistribution reaction depends on the stoichiometry of the reaction, as well as on the temperature. By way of example, it is possible to indicate that it will be of the order of 1 to 3 hours.

Before introducing the inhibitor, the reaction mixture is returned to atmospheric pressure, if needs be, for example by degassing.

The rate of introduction of the inhibitor silicone compound is not critical and it can be carried out, depending on the amount to be introduced, over a short period ranging, for example, from one minute to several minutes or over a longer period ranging, for example, from about ten minutes to several tens of minutes. The incorporation of the inhibitor compound generally results in a slight rise in temperature.

The stage which follows is thus the distillation, preferably at atmospheric pressure, which results in a distillate comprising the desired redistribution chlorinated organohydrosilane and a two-phase or homogenous distillation residue, depending on the amount of inhibitor silicone compound employed.

As regards the two types of silanes allowed to react, that is to say the chlorinated organohydrosilane of formula (1) and the organosubstituted and optionally chlorinated silane of formula (2), it will be noted that the R and R' symbols can be chosen, for example, from methyl, ethyl, propyl, isopropyl, butyl, hexyl, phenyl, naphthyl and diphenyl radicals.

The R and R' symbols are preferably alike or different and each represent a linear or branched $C_1$–$C_3$ alkyl radical or a phenyl radical.

In any case, the R and R' symbols which are very especially preferred are alike or different and each represent a methyl or a phenyl.

The method according to the present invention applies well to the implementation of a redistribution reaction between the chlorinated organohydrosilane (1) of formula $RHSiCl_2$ and the organosubstituted and chlorinated silane (2) of formula $R'_3SiCl$ (in this case, a=1, b=1 and c=3), in which formulae the R and R' symbols have the general meanings given above, in the presentation of the invention, with respect to the formulae (1) and (2).

The method according to the present invention applies very particularly well to the implementation of a redistribution reaction between the chlorinated organohydrosilane (1) of formula $RHSiCl_2$ and the organosubstituted and chlorinated silane (2) of formula $R'_3SiCl$ (in this case, a=1, b=1 and c=3), in which formulae the R and R' symbols are alike or different and each represent a linear or branched $C_1$–$C_3$ alkyl radical or a phenyl radical.

The method according to the present invention applies very especially well to the implementation of a redistribution reaction between the chlorinated organohydrosilane (1) of formula $RHSiCl_2$ and the organosubstituted and chlorinated silane (2) of formula $R'_3SiCl$, in which formulae the R and R' symbols are alike or different and each represent a methyl or phenyl radical.

Generally, in carrying out the method according to the present invention, the reactant of chlorinated organohydrosilane type of formula (1) can be present in the medium of the redistribution reaction in a proportion of at least 10 mol % with respect to the mixture: chlorinated organohydrosilane of formula (1)+organosubstituted and optionally chlorinated silane of formula (2).

Preferably, the molar ratio:

$$\frac{\text{chlorinated organohydrosilane of formula (1)}}{\text{organosubstituted silane of formula (2)}}$$

is between 0.1 and 2. More preferably still, this molar ratio is between 0.2 and 1.2 and very advantageously between 0.3 and 1.

In the context of the redistribution reaction, to the implementation of which the method according to the invention applies very especially well, for example involving $MeHSiCl_2$ and $Me_3SiCl$ as starting silanes (1) and (2), at the end a chlorinated organohydrosilane produced by redistribution, consisting of $Me_2HSiCl$, and the compound $Me_2SiCl_2$ are recovered. It should be noted that this silane $Me_2SiCl_2$ is essentially a product of the redistribution reaction but it can also originate, when it takes place, from the dismutation side reaction which has been spoken of above, where a portion of the redistributed silane $Me_2HSiCl$ is converted to $Me_2SiH_2$ and $Me_2SiCl_2$.

The method according to the invention makes it possible to significantly increase the yields of redistributed chlorinated-organohydrosilane (for example $Me_2HSiCl$), while simplifying the synthetic operating procedures (redistribution/distillation).

The devices used for the implementation of the method are conventional chemical engineering devices entirely within the scope of a person skilled in the art.

The examples which follow will make it possible to better understand all the alternative forms and the advantages (processability) of the method according to the invention by underlining, by comparative tests, the increases in yield obtained.

EXAMPLES

A) Inhibitor silicone compounds employed:
SIL 1: alkoxysilane of formula: $(C_6H_5)_2Si(OC_2H_5)_2$;
SIL 2: alkoxysilane of formula: $MeSi(OC_2H_5)_3$.
B) Procedure:
(I) Tests Without Locking Up of Catalyst:

Comparative Example 320 g of $Me_3SiCl$ and 171 g of $MeHSiCl_2$, in order to obtain an $MeH/Me_3$ molar ratio equal to 0.505, are charged with stirring to a 750 ml stainless steel reactor purged beforehand with nitrogen. The catalyst, i.e. 15 g of anhydrous aluminium chloride, is added to this mixture. The reactor is closed and the pressure is adjusted to $10 \times 10^5$ Pa with nitrogen and to the value of atmospheric pressure. Stirring is provided by a cavitation turbomixer. The stirring speed is set at 1500 revolutions/min. Heating is carried out to 100° C. and the pressure settles down at around 4 to $5 \times 10^5$ Pa. The temperature is maintained at 100° C. for 2 hours. The reactor is cooled to 20° C. and the residual pressure of 1.5 to $2 \times 10^5$ Pa is removed by degassing. 473 g of the reaction mixture, comprising 68.6 g of $Me_2HSiCl$ and 3% by weight of aluminium chloride, are separated by distillation at atmospheric pressure. A distillate comprising the dimethylhydrochlorosilane and a heterogeneous distillation residue with suspended $AlCl_3$ are obtained.

The distillates and residues are analysed by vapour phase chromatography. $Me_2HSiCl$ in distillate: 48.4 g.

II) Tests With Locking Up of Catalyst:

Example 1

320 g of $Me_3SiCl$ and 171 g of $MeHSiCl_2$, in order to obtain an $MeH/Me_3$ molar ratio equal to 0.505, are charged with stirring to a 750 ml stainless steel reactor purged beforehand with nitrogen.

The catalyst, i.e. 15 g of anhydrous aluminium chloride, is added to this mixture. The reactor is closed and the pressure is adjusted to $10 \times 10^5$ Pa with nitrogen and then to atmospheric pressure. Stirring is provided by a cavitation turbomixer. The stirring speed is set at 1500 revolutions/min. Heating is carried out to 100° C. and the pressure settles down at around 4 to $5 \times 10^5$ Pa. The temperature is maintained at 100° C. for 2 hours. 30 g of inhibitor compound SIL 1 are subsequently introduced into the reactor over a period of approximately 2 minutes. The reactor is subsequently cooled to 20° C. The residual pressure of 1.5 to $2 \times 10^5$ Pa is removed by degassing. 500 g of reaction mixture, comprising 68.6 g of $Me_2HSiCl$ and the inactive catalyst, are separated by distillation at atmospheric pressure. A distillate comprising the dimethylhydrochlorosilane and a homogeneous two-phase distillation residue are obtained.

The distillates and residues are analysed by vapour phase chromatography. $Me_2HSiCl$ in distillate: 68 g.

Example 2

320 g of $Me_3SiCl$ and 171 g of $MeHSiCl_2$, in order to obtain an $MeH/Me_3$ molar ratio equal to 0.505, are charged with stirring to a 750 ml stainless steel reactor purged beforehand with nitrogen.

The catalyst, i.e. 15 g of anhydrous aluminium chloride, is added to this mixture. The reactor is closed and the pressure is adjusted to $10 \times 10^5$ Pa with nitrogen and then to atmospheric pressure. Stirring is provided by a cavitation turomixer. The stirring speed is set at 1500 revolutions/min. Heating is carried out to 100° C. and the pressure settles down at around 4 to $5 \times 10^5$ Pa. The temperature is maintained at 100° C. for 2 hours. 15 g of inhibitor compound SIL 1 are introduced into the reactor over a period of approximately 2 minutes. The reactor is subsequently cooled to 20° C. The residual pressure of 1.5 to $2 \times 10^5$ Pa is removed by degassing. 485 g of reaction mixture, comprising 68 g of $Me_2HSiCl$ and the inactive catalyst, are separated by distillation at atmospheric pressure. A distillate comprising the dimethylhydrochlorosilane and a homogeneous distillation residue are obtained.

The distillates and residues are analysed by vapour phase chromatography. $Me_2HSiCl$ in distillate: 65.2 g.

Example 3

320 g of $Me3SiCl$ and 171 g of $MeHSiCl_2$, in order to obtain an $MeH/Me_3$ molar ratio equal to 0.505, are charged with stirring to a 750 ml stainless steel reactor purged beforehand with nitrogen.

The catalyst, i.e. 15 g of anhydrous aluminium chloride, is added to this mixture. The reactor is closed and the pressure is adjusted to $10 \times 10^5$ Pa with nitrogen and then to atmospheric pressure. Stirring is provided by a cavitation turbomixer. The stirring speed is set at 1500 revolutions/min. Heating is carried out to 100° C. and the pressure settles down at around 4 to $5 \times 10^5$ Pa. The temperature is maintained at 100° C. for 2 hours. 6.7 g of inhibitor compound SIL 2 are introduced into the reactor over a period of approximately 2 minutes. The reactor is subsequently cooled to 20° C. The residual pressure of 1.5 to $2 \times 10^5$ Pa is removed by degassing. 477 g of reaction mixture, comprising 68.5 g of $Me_2HSiCl$ and the inactive catalyst, are separated by distillation at atmospheric pressure. A distillate comprising the dimethylhydrochlorosilane and a homogeneous distillation residue are obtained.

The distillates and residues are analysed by vapour phase chromatography. $Me_2HSiCl$ in distillate: 56 g.

Example 4

320 g of $Me_3SiCl$ and 171 g of $MeHSiCl_2$, in order to obtain an $MeH/Me_3$ molar ratio equal to 0.505, are charged with stirring to a 750 ml stainless steel reactor purged beforehand with nitrogen.

The catalyst, i.e. 15 g of anhydrous aluminium chloride, is added to this mixture. The reactor is closed and the pressure is adjusted to $10 \times 10^5$ Pa with nitrogen and then to atmospheric pressure. Stirring is provided by a cavitation turbomixer. The stirring speed is set at 1500 revolutions/min. Heating is carried out to 100° C. and the pressure settles down at around 4 to $5 \times 10^5$ Pa. The temperature is maintained at 100° C. for 2 hours. 15 g of inhibitor compound SIL 2 are introduced into the reactor over a period of approximately 2 minutes. The reactor is subsequently cooled to 20° C. The residual pressure of 1.5 to $2 \times 10^5$ Pa is removed by degassing. 486 g of reaction mixture, comprising 68.3 g of $Me_2HSiCl$ and the inactive catalyst, are separated by distillation at atmospheric pressure. A distillate comprising the dimethylhydrochlorosilane and a homogeneous distillation residue are obtained.

The distillates and residues are analysed by vapour phase chromatography. $Me_2HSiCl$ in distillate: 68 g.

The results obtained are summarized in the following Table I. RY represents the yield of the distillation.

| Examples | Catalyst AlCl₃ Weight (g) | Catalyst AlCl₃ Mole of Al atoms | Inhibitor Inhibitor nature | Inhibitor Weight (g) | Inhibitor Mole of OR² groups | Molar ratio r | Me₂HSiCl (*) | Look of the residue H = homogeneous T = two-phase |
|---|---|---|---|---|---|---|---|---|
| Comparative Ex. 1 | 15 | 0.112 | none | | | | 70.6 | T |
| Example 1 | 15 | 0.112 | SIL 1 | 30 | 0.220 | 0.51 | 99.1 | H |
| Example 2 | 15 | 0.112 | SIL 1 | 15 | 0.110 | 1.02 | 95.9 | H |
| Example 3 | 15 | 0.112 | SIL 2 | 6.7 | 0.114 | 0.98 | 81.8 | H |
| Example 4 | 15 | 0.112 | SIL 2 | 15 | 0.252 | 0.44 | 99.6 | H |

(*) distillation yield in %

What is claimed is:

1. Improved method for obtaining organosilanes comprising:

a redistribution reaction between a chlorinated organohydrosilane of formula (1) $(R)_a(H)_bSiCl_{4-a-b}$ and an organosubstituted and optionally chlorinated silane of formula (2) $(R')_cSiCl_{4-c}$, in which formulae: a=1 or 2; b=1 or 2; a+b≦3; c=1, 2, 3 or 4; and the symbols R and R' are alike or different and each represent a linear or branched $C_1$–$C_6$ alkyl radical or a $C_6$–$C_{12}$ aryl radical; said redistribution reaction taking place in the presence of an effective amount of a catalyst consisting of a Lewis acid of formula (3) $M(X)_d$, in which: M represents a metal selected from Ti, Fe, Cu, Ag, Zn, Cd, Hg, Al, Ga, In, B, Sn, Pb, Sb and Bi; X represents a halogen atom; and d represents the valency of the metal M;

and a separation by distillation of the chlorinated orga-nohydrosilane produced by redistribution; said method being characterized in that, after the redistribution, at least one compound which inhibits the redistribution catalyst is introduced, this compound corresponding to the following definitions:

it comprises:

(i) a silane of formula:

in which:

the $R^1$ symbols are alike or different and each represent: a hydrogen atom; a linear or branched $C_1$–$C_8$ alkyl radical optionally substituted by one or more halogen(s); a $C_5$–$C_8$ cycloalkyl radical; a $C_6$–$C_{12}$ aryl radical or an aralkyl radical having a $C_6$–$Cl_2$ aryl part and a $C_1$–$C_4$ alkyl part which is optionally substituted on the aromatic part by one or more halogen(s), $C_1$–$C_3$ alkyl(s) and/or $C_1$–$C_3$ alkoxy(s);

the $R^2$ symbols are alike or different and each represent: a linear or branched $C_1$–$C_4$ alkyl radical; or a $C_6$–$C_{12}$ aryl radical;

e is 0, 1, 2 or 3;

(2i) a silicone resin having a viscosity at 25° C. at most equal to 5000 mpa·s and exhibiting the following distinctive features:

it has, in its structure, units chosen from those of formulae $(R^3)_3SiO0.5$ (M), $(R^3)_2SiO$ (D), $R^3SiO_{1.5}$ (T) and $SiO_2$ (Q), at least one of these units being a T unit or a Q unit, in which formulae the $R^3$ symbols, which are alike or different, mainly have the definitions given above with respect to the $R^1$ symbols;

the proportions of the T and/or Q units, expressed by the number of T and/or Q units per 100 silicon atoms, are greater than 10%;

it also possesses, per molecule, —$OR^4$ end groups carried by silicon atoms of the M, D and/or T units, where:

the $R^4$ symbols, which are alike or different, each represent a hydrogen atom, a linear or branched $C_1$–$C_4$ alkyl radical or a $C_6$–$C_{12}$ aryl radical, the proportions of the —$OR^4$ ends, expressed by the mean number of these ends per 1 silicon atom, vary from 0.2 to 3;

it is used in proportions such that the ratio:

$$r = \frac{\text{number of moles of } M \text{ metal atoms contributed by the catalyst}}{\text{number of moles of } OR^2 \text{ or } OR^4 \text{ groups contributed by the inhibitor}}$$

is equal to or less than 1.1.

2. Method according to claim 1, wherein the inhibitor silicone compound is used in proportions such that r is situated within the range from 0.4 to 1.1.

3. Method according to claim 1, wherein the inhibitor silicone compounds are:

as silanes (i): the alkoxysilanes of formula (4) in which:

the $R^1$ symbols, which are identical, each represent a linear or branched $C_1$–$C_4$ alkyl radical or a phenyl radical;

the $R^2$ symbols, which are identical, each represent a linear or branched $C_1$–$C_3$ alkyl radical;

e=1 or 2;

as resins (2i): the resins having a viscosity at 25° C. at most equal to 1000 mPa·s ot MQ, MDQ, TD and MDT type, in the structure of which:

the $R^3$ symbols of the M, D and T units are alike or different and each represent a linear $C_1$–C, alkyl radical;

the proportions of the T and/or Q units are greater than 30%;

there are —$OR^4$ end groups where the $R^4$ symbol represents a hydrogen atom or a linear $C_1$–$C_2$ alkyl radical and where the proportions of said ends vary from 0.3 to 2.

4. Method according to claim 3, wherein the inhibitor silicone compounds are:

the alkoxysilanes (i) corresponding to the following

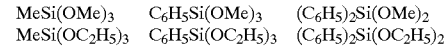

the resins (2i) of TD type, in the structure of which:

the $R^3$ symbols of the D units are methyl radicals, whereas the $R^3$ symbols of the T units are n-propyl radicals;

the proportions of the T units, expressed by the number of T units per 100 silicon atoms, lie within the range from 40 to 65% and those of the D units, expressed by the number of D units per 100 silicon atoms, lie within the range from 60 to 35%;

the —$OR^4$ end groups, where the $R^4$ symbol represents an ethyl radical, are carried by silicon atoms of the D and T units and are present in proportions ranging from 0.3 to 0.5.

5. Method according to claim 1, wherein the Lewis acids which are employed as catalysts are chlorides and bromides.

6. Method according to claim 5, wherein the catalyst comprises $TiCl_4$, $FeCl_3$, $CuCl$, $AgCl$, $ZnCl_2$, $AlCl_3$, $SnCl_2$, $BiCl_3$ or their various mixtures.

7. Method according to claim 1, wherein the catalyst is used in proportions by weight ranging from 0.1 to 10% by weight with respect to the total weight of the silanes of formulae (1) and (2) charged at the start.

8. Method according to claim 1, wherein:

carrying out the redistribution reaction at a temperature of between 50° C. and 200° C., subsequently cooling the reaction mixture to a temperature of less than 40° C., introducing the inhibitor silicone compound, and, finally, separating the targeted chlorinated organohydrosilane, produced by redistribution, by distillation.

9. Method according to claim 1, wherein:

carrying out the redistribution at a temperature of between 50 and 200° C., introducing the inhibitor silicone compound, so that the redistribution is interrupted, subsequently cooling the reaction mixture to a temperature of less than 40° C., and, finally, separating the targeted chlorinated organohydrosilane by distillation.

10. Method according to claim 1 to 9, wherein the chlorinated organohydrosilane of formula (1) and the organosubstituted and optionally chlorinated silane of formula (2), the R and R' symbols are alike or different and each represent a linear or branched $C_1$–$C_3$ alkyl radical or a phenyl radical.

11. Method according to claim 1, wherein a redistribution reaction is carried out between the chlorinated organohydrosilane (1) of formula $RHSiCl_2$ and the organosubstituted and chlorinated silane (2) of formula $R'_3SiCl$.

12. Method according to claim 1 to 11, wherein the molar ratio:

$$\frac{\text{chlorinated organohydrosilane of formula (1)}}{\text{organosubstituted silane of formula (2)}}$$

* * * * *